United States Patent [19]
Georgevich

[11] Patent Number: 5,200,317
[45] Date of Patent: Apr. 6, 1993

[54] METHOD AND DEVICE FOR QUANTITATIVE CHROMATOGRAPHY

[75] Inventor: Gradimir G. Georgevich, Mundelein, Ill.

[73] Assignee: Abbott Laboratories, Abbott Park, Ill.

[21] Appl. No.: 821,280

[22] Filed: Jan. 10, 1992

Related U.S. Application Data

[63] Continuation of Ser. No. 305,886, Feb. 2, 1989.

[51] Int. Cl.[5] .................. G01N 33/543; G01N 31/78; C12Q 1/42
[52] U.S. Cl. ...................................... 435/7.4; 435/21; 436/518; 422/56; 422/57
[58] Field of Search ................ 435/21, 7.4; 436/518; 422/56, 57, 21

[56] References Cited

U.S. PATENT DOCUMENTS

| | | | |
|---|---|---|---|
| 3,699,005 | 10/1972 | Foster et al. | |
| 3,905,872 | 9/1975 | Forgione | 435/12 |
| 3,915,647 | 10/1975 | Wright | 23/253 TP |
| 4,059,407 | 11/1977 | Hochstrasser | 23/253 TP |
| 4,168,146 | 9/1979 | Grubb et al. | 23/230 B |
| 4,298,688 | 11/1981 | Kallies | 435/14 |
| 4,435,504 | 3/1984 | Zuk et al. | 435/7 |
| 4,446,232 | 5/1984 | Liotta | 435/7 |
| 4,555,484 | 11/1985 | LaRossa et al. | 435/21 |
| 4,740,468 | 4/1988 | Weng et al. | 435/7 |

Primary Examiner—Christine M. Nucker
Assistant Examiner—M. P. Woodward
Attorney, Agent, or Firm—Thomas D. Brainard; Daniel R. Curry

[57] ABSTRACT

An improved chromatographic device and method for quantitating the activity of an enzyme utilizes a bibulous test strip as the stationary phase, an aqueous solution as the mobile phase, and a chromophore as the indicator. The enzyme activity is quantitated by transforming a substantially depletable amount of a chromogenic substrate from soluble chromogen to insoluble chromophore as the mobile phase advances, whereupon the insoluble chromophore becomes immobilized on the test strip to produce a column of color. The length and/or the intensity of the column of color are related to the activity of the enzyme. The present invention is useful for the direct determination of enzyme-analytes and for the indirect determination of analytes which can be coupled to an enzyme.

15 Claims, 2 Drawing Sheets

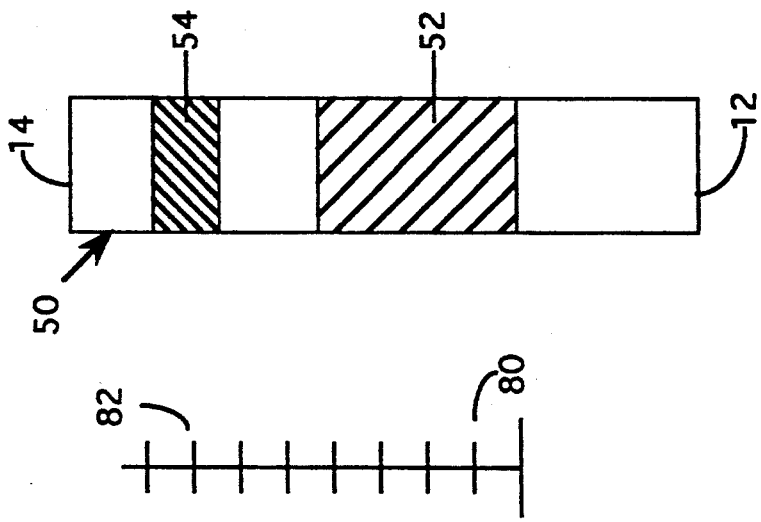
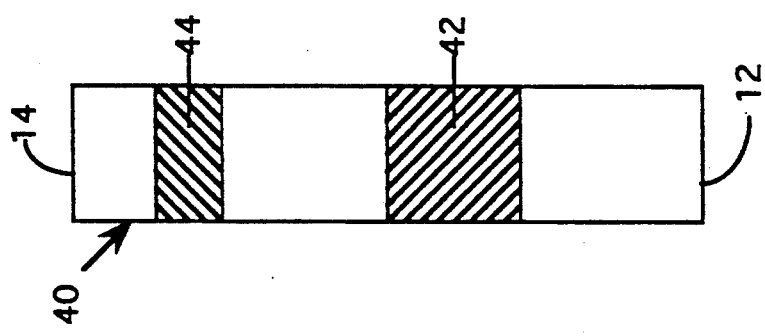
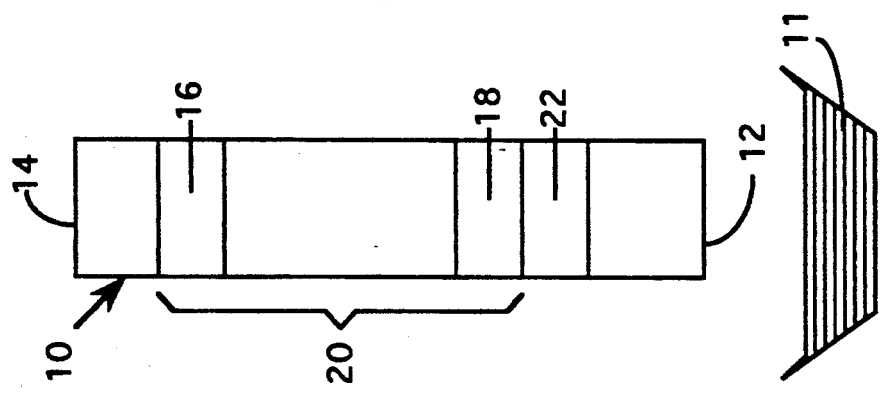

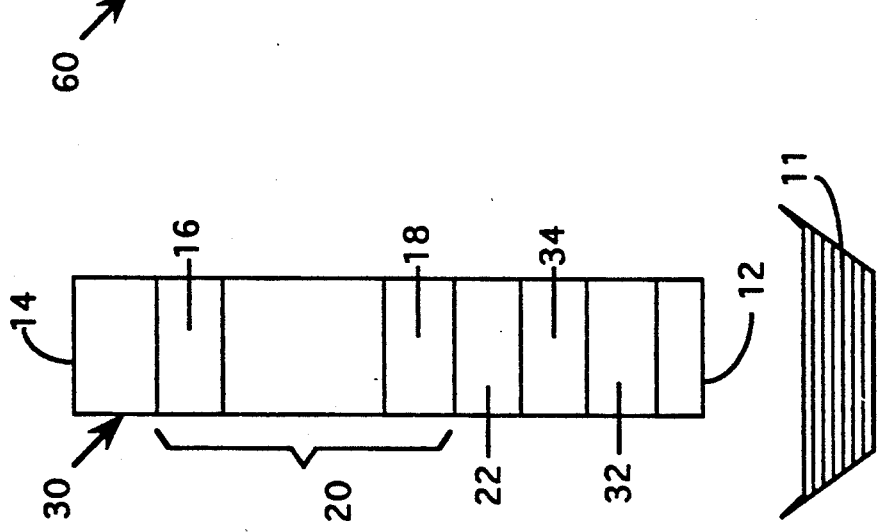
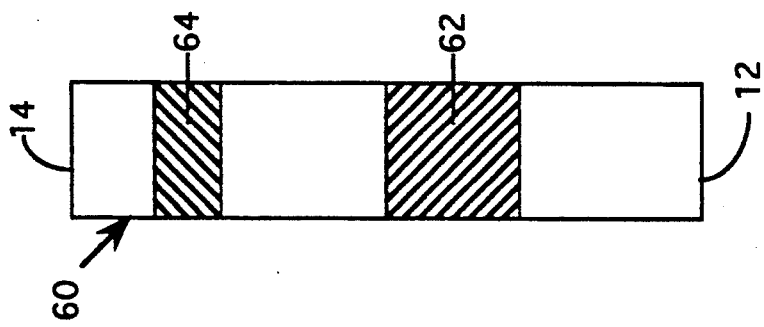
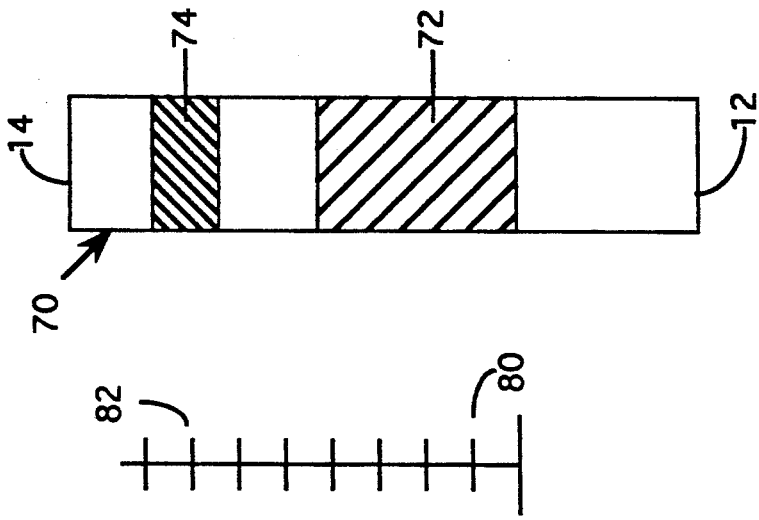

METHOD AND DEVICE FOR QUANTITATIVE CHROMATOGRAPHY this application is a continuation of application Ser. No. 07/305,886, filed Feb. 2, 1989.

BACKGROUND OF THE INVENTION

The present invention relates to a method and device for quantifying the activity of an enzyme using a chromatographic test strip. More particularly, the present invention quantitates enzyme activity by transforming a substantially depletable amount of a chromogenic substrate from soluble chromogen to insoluble chromophore as the mobile phase advances, whereupon the insoluble chromophore becomes immobilized on the test strip to produce a column of color. The length and/or the intensity of the column of color are related to the activity of the enzyme. The present invention is useful for the direct determination of enzyme analytes and for the indirect determination of analytes which can be coupled to enzymes.

The prior art contains numerous examples of chromatographic methods for quantitating an analyte. See, for example, U.S. Pat. Nos. 4,298,688 (Kallies); 4,059,407 (Hochstrasser); 4,168,146 (Grubb); and 4,435,504 (Zuk). All of these examples employ soluble chromogens which are converted to soluble chromophores.

Soluble chromophores present numerous problems to the development of a quantitative chromatographic assay; namely they advance as a narrow line with the migrating solvent front, making quantitation impossible. To avoid this problem and produce a quantitative chromatographic assay, chromatographic assays were produced wherein the chromophore was developed only after migration had occurred. Although these assays avoid the migration problem, they require multi-step procedures.

Another problem with soluble chromophores is that they tend to diffuse over time. Hence, the measurement of any color must be precisely timed, particularly if the distance traveled by the color is to be proportional to the quantity of analyte present. In addition, conventional reaction kinetics dictate that results be read at a precise time during development.

Copending and co-owned application Ser. No. 118,148 filed Nov. 6, 1987 discloses a method of quantitating enzyme activity employing a chromatographic strip device. A sample containing enzyme is immobilized at a reaction site on the strip and a solution of substrate/cofactors is transported over the site to form a reaction product which is transported to a detection region beyond. The rate of reactant consumption or product formation is then determined.

Others have attempted to solve soluble chromophore problems by employing dipstick tests which do not require a mobile aqueous phase. These devices have a plurality of reagents contained therein in distinct zones (i.e. layers). Application of the sample to the test device causes the reagents to dissolve and mix uniformly over the dipstick. Color is uniformly distributed over the surface of the test device. Quantitation, if possible at all, can be done only by comparison against a standard or by instrumentation capable of reflectance or transmission spectrophotometry.

SUMMARY OF THE INVENTION

The present invention provides a single step method and a device for the quantitative chromatographic analysis of enzyme activity. The enzyme may be the analyte itself, or it may be a label coupled to the analyte of interest.

In one aspect, the present invention is directed to an improved chromatographic solid phase device for quantitating the activity of an enzyme in a sample. The device comprises a bibulous test strip having a proximal end and a distal end, the proximal end for receiving a test sample in an aqueous mobile phase. Disposed between the proximal and distal ends is a substrate zone incorporating a fixed, substantially depletable amount of a transformable enzyme substrate. The substrate must be soluble in the aqueous test sample and, upon transformation by the enzyme, become immobilized on the bibulous test strip to generate a detectable signal, such as color.

A quantitation zone is disposed between said substrate zone and the distal end whereby, as the mobile phase advances over the strip, the transformed, immobilized substrate produces a column of signal, the amount of signal being related to the activity of said enzyme. Typically, the signal is a chromophore (preferably insoluble) so that the length or intensity of a column of color can be measured and related to the enzyme activity.

In another aspect, the invention provides a method of quantitating the activity of an enzyme, comprising the steps of (a) contacting the proximal end of the bibulous test strip described above with an aqueous test sample and allowing the aqueous test sample to migrate to the quantitation zone, and (b) determining the amount of signal produced there as a measure of the enzyme activity.

Finally, a method of quantitating an analyte comprises quantitating the activity of an enzyme label which is conjugated to the analyte directly or indirectly, and relating the enzyme activity to the amount of analyte.

DESCRIPTION OF THE FIGURES

FIG. 1 discloses the substrate and quantitation zones in a chromatographic device of the present invention wherein an enzyme is the analyte of interest.

FIG. 2A shows the embodiment of FIG. 1 in response to a sample containing a high concentration of enzyme.

FIG. 2B shows the embodiment of FIG. 1 in response to a sample containing a low concentration of enzyme.

FIG. 3 discloses an embodiment of the present invention wherein the enzyme is a label bound to the analyte of interest.

FIG. 4A shows the embodiment of FIG. 3 in response to a sample containing a high concentration of analyte.

FIG. 4B shows the embodiment of FIG. 3 in response to a sample containing a low concentration of analyte.

DETAILED DESCRIPTION

The present invention relates to an improved chromatographic method and device for quantifying the activity of an enzyme. The method and device of the present invention employ a bibulous test strip as a solid stationary phase, an aqueous solution as a mobile phase, and a substantially depletable amount of a transformable substrate which initially is solubilized by the aqueous phase and, upon transformation, becomes immobilized and generates a signal.

Two embodiments of the device of the present invention are shown in FIGS. 1 and 3. The bibulous test strips 10, 30 each have a proximal end 12 and a distal end 14. The proximal end 12 is the receiving end at which the test sample is applied and from where chromatographic migration begins. The distal end 14 is where migration stops.

Optionally, the distal end 14 may contain an indicator zone 16 impregnated with a reagent which indicates when migration is complete as shown in FIGS. 2A, 2B, 4A and 4B by numerals 44, 54, 64 and 74, respectively. Indicator reagents which change color upon contact with the mobile phase are suitable for this zone. Dehydrated transition metal salts such as $CuSO_4$ or $Co(NO_3)_2$, which change color when hydrated, are suitable for aqueous mobile phases. Especially preferred are the pH indicator dyes (e.g. phenolphthalein) which can be selected to change color in response to the (buffered) mobile phase.

The "bibulous test strip" 10, 30 is any porous matrix possessing capillarity through which an aqueous solution containing the analyte may pass. Materials suitable for use as a bibulous test strip include various cellulose fiber containing matrices such as filter papers, chromatographic papers, ion exchange papers, cellulose acetate films, nitrocellulose films, cellulose acetate discs, cellulose thin layer chromatography discs and the like. Additional suitable materials for the bibulous test strip include starch based materials, such as Sephadex(®) brand cross-linked dextran chains, and other materials such as ceramic materials, glass fibers, films of polyvinyl chloride, and combinations of polyvinyl chloride and silica. Especially preferred are bibulous test strips wherein the matrix material is glass fiber.

Although the thickness of the bibulous test strip may vary depending upon the size of the sample, the preferred thickness is from 0.1 to 1.0 mm. The test strip 10, 30 may be adhered to and supported by a water insoluble physical support (not shown) if desired.

The aqueous mobile phase may be the sample itself or, more preferably, a buffered wicking solution 11 containing the sample. The sample is preferably a biological fluid extracted, diluted, or concentrated from a plant or animal. Exemplary biological fluids are serum, plasma, urine, ascites fluid, peritoneal fluid, amniotic fluid, synovial fluid, cerebrospinal fluid and the like.

The buffered wicking solution comprises an aqueous solution which may contain miscible organic solvents such as lower alkyl alcohols, acetone and the like. The function of the wicking solution 11 is to transport the sample across the length of the bibulous test strip 10, 30 by capillary action. The wicking solution may contain buffers to maximize the chemical and/or immunochemical activity of the other components. More preferably, however, buffers, cofactors, surfactants, enzyme activators and other desirable components are impregnated in an additional zone or zones (e.g. 22 and 32) which are discussed in more detail below.

The substrate zone 18 contains a fixed, substantially depletable amount of a transformable enzyme substrate. It is an important aspect of the invention that the substrate be transformable. By "transformable" is meant having the ability to be converted by an enzyme from a substrate which is soluble in the mobile phase to a product/signal compound (transformed substrate) which is immobilized on the bibulous test strip of the solid phase. Thus, "transformation" comprehends both signal generation and immobilization. Matrices, substrates and wicking solutions are chosen so as to optimize transformation.

Preferably, the signal compound generates a signal which can be detected visually. For example, it is preferred that the transformable substrate is chromogenic (a precursor), while the product (transformed substrate) is a chromophore. However, fluorescent and other signals are within the scope of the present invention, provided they generate a detectible signal and become immobilized upon transformation by an enzyme.

The specific substrate chosen for the substrate zone 18 depends on the enzyme whose activity is to be determined. One of ordinary skill in the art can easily determine a transformable substrate for a given enzyme. For example, the various alkaline and acid phosphatases can be determined with the transformable substrate 3-indoxyl phosphate (Sigma Chemical Co., St Louis #I 5505); $\beta$-D-glucosidase can be determined with the transformable substrate 3-indoxyl-$\beta$-D-glucoside (Sigma Chemical Co., St Louis); and the aryl sulfatase enzymes can be determined with the transformable substrate 3-indoxyl-sulfate (Sigma Chemical Co., St Louis #I 3875). Finally, $\beta$-galactosidase could be determined with a transformable substrate such as 3-indoxyl-$\beta$-D-galactoside.

Similarly, the fixed amount which constitutes a substantially depletable quantity also depends on the enzyme whose activity is to be determined, as well as the assay configuration. Where the enzyme is the analyte of interest, the amount of substrate should be that quantity which will be substantially totally transformed by a given aliquot of sample having an enzyme concentration at the low end of the clinically anticipated range. Where the enzyme is a label, the amount of substrate should be that quantity which will be substantially totally transformed by the minimum amount of analyte:label conjugate reaching the quantitation zone. This, in turn, is governed by the specific analyte, the sample aliquot, the capture zone configuration and other conditions. One of ordinary skill in the art can easily determine an appropriate amount of transformable substrate for a given enzyme. Some specific examples are provided later in this specification.

Immobilization of transformed substrate on the bibulous strip encompasses both covalent immobilization and physical immobilization. In the first case, covalent immobilization can be achieved through known reactions such as linkers or derivatization of the matrix. An example of this latter approach can be found in copending U.S. application Ser. No. 204,443, assigned to the same assignee as the present application and incorporated herein by reference.

Physical immobilization can be achieved through adsorption or solubility and is preferred for the present invention. A substrate is selected so that it is solubilized by migration of the aqueous mobile phase and, when transformed to the product/signal compound, is relatively insoluble in the same mobile phase. Solubilization initially releases substrate that has been impregnated or deposited, such as by drying or lyophilization, into the substrate zone 18. Typically, insolubility in aqueous phases is induced (through transformation by the enzyme) by removal or blocking of a polar group.

The quantitation zone 20 begins where the enzymatic reaction first begins to transform the soluble transformable substrate into signal compound. Accordingly, the zone that provides the last critical reactant to the enzymatic transformation marks the starting point of the quantitation zone 20. Since the last critical reactant typically is the solulizable transformable enzyme substrate, the quantitation zone 20 overlaps the substrate zone 18. This overlap is evident from a side by side comparison of the drawing Figures.

The substantially depletable amount of substrate is a fixed quantity of substrate which the enzyme will transform at a rate proportional to the activity of the enzyme. Thus, the more enzyme activity present, the faster the substrate is depleted, as shown at 42 and 62 in FIGS. 2A and 4A. Conversely, the less enzyme activity present, the slower the rate of transformation, as shown at 52 and 72 in FIGS. 2B and 4B. There is a fixed quantity of substrate to be depleted, so the amount of signal formed is constant. Quantitation is achieved through the time required for the unknown enzyme activity to transform all the substrate to signal.

This time period is translated to intensity and length of the column of signal by the migration of the mobile phase. Although the wicking rate of the advancing solvent front is not absolutely constant, given a homogeneous matrix material and a constant viscosity and temperature, the rate of wicking is predictable. Depletion of the substrate tends to slow the kinetics of transformation by the enzyme. At the same time, the wicking rate slows as the front moves toward the distal end 14. Thus, transformation of substrate (and therefore enzyme activity) is related both to the intensity of the signal and, more importantly, to the length of the column of signal produced.

This is advantageous in that the need for an external timing element is eliminated. Unlike conventional dipstick assays, the time at which the result is read is not critical. Timing is achieved by migration and solvent depletion, to make quantitation possible. The exact mechanics of quantitation depend on the assay configuration and are discussed separately below.

Although FIGS. 1 and 3 illustrate various embodiments of the device of the present invention, the relative length of the various zones shown therein are for illustrative purposes only. In actual practice, the length of the individual zones may vary depending upon such factors as amount and solubility of the components and the function provided by the zone. In its shortest form, a zone can be merely a line (not shown) extending across the width of the bibulous test strip 10, 30. Indicator zone 16 is preferably of sufficient length to provide a visible indication that migration has been completed.

The length of the column of signal can be compared to a predetermined scale 80 having gradations 82 corresponding to enzyme or analyte concentration. The scale 80 may be incorporated (not shown) into the test strip 10, 30. Alternatively, it may be separate and form a part of a kit, The scale 80 may comprise a portion of a box or carton containing the device.

Zones 22 are optional accessory zones. One or more of these zones may be present and contain surfactants, buffers, enzyme cofactors, enzyme activators or other components desirable for the wicking solution. Typically the zone 22 immediately proximal to the substrate zone 18 contains buffers and other components that optimize the activity of the enzyme of interest. For example, if the enzyme is alkaline phosphatase, zone 22 should contain at least a buffer at about pH 9.4 to 10.5, preferably pH 9.8, and a phosphate acceptor. Wicking solution conditions, particularly pH, can be adjusted to alter the activity of the enzyme in order to increase the dynamic range.

Illustrative buffers include phosphate, carbonate, barbital, diethylamine, tris, 2-amino-2-methyl-1-propanol (AMP) and the like. Although the particular buffer employed is not usually critical, in certain instances it may be. For example, a phosphate buffer should not be used when analyzing for acid or alkaline phosphatase activity.

It is also contemplated that the accessory zones 22 could be separated from the substrate zones 18 by regions having no reactants, or placed distal to the substrate zones as taught by U.S. Pat. No. 4,555,484.

Part or all of the device may be coated with a protectant such as fish gelatin.

A. Enzyme Analyte

The embodiment presented in FIG. 1 is particularly suited to quantitating the concentration of an enzyme as an analyte of interest. Under given conditions, the activity of an enzyme is proportional to the concentration of the enzyme in the sample. Activity is determined according to the invention. Typical enzyme/analytes include alkaline phosphatase, acid phosphatase, SGOT, SGPT, and other enzymes for which a particularly low or high level, alone or in combination with other information, is clinically indicative of a disease state.

In particular, FIG. 2A discloses a bibulous test strip 40, like that of FIG. 1, after migration of a test sample containing a high concentration of enzyme. The column of color 42 is very short and intense since the high concentration of enzyme produces substrate depletion early in the migration. As a result of high enzyme activity, the transformed substrate is immobilized more rapidly. Since a fixed, depletable quantity was present initially, the column is produced over a shorter distance during the migration and is relatively intense. In contrast, FIG. 2B shows a bibulous test strip 50 after migration of a test sample containing a low concentration of enzyme. The column of color 52 is relatively long and less intense, since the low concentration of enzyme took a longer time to deplete the substrate. Thus, transformed substrate (chromophore) is immobilized over a greater distance.

Quantitation of enzyme activity can be accomplished by measuring the length or intensity of the column of signal 42, 52. In the embodiment of FIG. 1, the length of the column of signal (preferably color) is inversely proportional to enzyme activity and concentration. Intensity of the column of signal, however, is directly proportional to enzyme activity and concentration.

B. Enzyme Label

An embodiment of the device 30 of the present invention suitable for quantitating an analyte when the enzyme constitutes a label is presented in FIG. 3. Typically, the enzyme is linked to a ligand or receptor capable of directly or indirectly binding the analyte of interest. The linked complex of enzyme:ligand is referred to herein as "conjugate". A number of methods are well known to those skilled in the art for preparing the conjugate complex. For antigenic analytes, the conjugate usually comprises enzyme:anti-analyte antibody. However, the conjugate may also comprise avidin, biotin, lectins, complementary DNA or RNA oligonucleotides, or other analyte specific ligands complexed with an enzymatic label.

The bibulous test strip 30 of FIG. 3 is divided into a conjugate zone 32, a capture zone 34, an accessory zone 22, a substrate zone 18, a quantitation zone 20 and an indicator zone 16. The substrate zone 18, the accessory zone 22 and the indicator zone 16 are substantially the same as those previously described, and, for the sake of brevity, will not be discussed in detail at this point. The quantitation zone 20 is the same in that columns of signal 62, 72 are produced. The relationship of the columns 62, 72 to the analyte depends on the capture zone 34 as discussed below.

In this embodiment, the conjugate zone 32 contains an excess of solulizable, analyte-specific conjugate. Methods for drying or impregnating conjugate into the zone 32 on the test strip 30 are known in the art. The conjugate is transferred to the mobile phase by dissolving therein during migration of the solvent front.

By varying the content of the capture zone 34, one of ordinary skill in the art can produce a column of signal whose length is either directly or inversely proportional to the analyte concentration. Capture zone 34 selectively passes conjugate to the substrate zone 18 in a manner related to the amount of analyte present. The capture zone 34 contains immobilized therein a reagent that captures conjugate directly or indirectly, so that the amount of conjugate enzyme activity passing through to the substrate zone 18 is related directly (direct conjugate capture) or inversely (indirect conjugate capture) to the amount of analyte present. By the mechanism previously described, the enzyme activity quantitated by the present invention is inversely related to the length of the column of signal and directly related to the intensity of the signal column. Thus, direct capture of conjugate results in an inverse relationship between column length and analyte concentration, while indirect capture of conjugated results in a direct relationship.

In a direct capture variation, the capture zone 34 contains a predetermined fixed quantity of immobilized analyte or analyte analog such as an antigen which serves to capture directly any antibody:enzyme conjugate mobilized by the solvent front which is not bound to analyte from the test sample. Only the conjugate not bound to analyte can advance with the solvent front to the quantitation zone 20. Accordingly, the greater the amount of analyte in the test sample, the greater the amount of conjugate to reach the quantitation zone. As with the first embodiment, increased amounts of enzyme produce shorter columns of color (e.g. 62), and hence an inverse relationship exists between the length of the column of color and the concentration of analyte in the test sample.

The length and content of the capture zone 34 contains sufficient capture reagent to capture substantially all the conjugate when the test sample happens to contain no analyte of interest. However, it is within the ordinary skill in the art to vary the length and amount of immobilized analyte or analyte analog in capture zone 34 so as to adjust the sensitivity of the device. For example, by placing a predetermined excess of immobilized analyte in zone 34, only those samples with analyte concentrations above a certain threshold will produce a column of color. Such an embodiment is particularly suited for screening for elevated concentrations of common serum analytes, e.g. cholesterol, TSH, SGOT, SGPT, alkaline phosphatase, acid phosphatase, etc., wherein an elevated concentration is associated with a particular disease state.

This variation is exemplified by Weng, et al., U.S. Pat. No. 4,740,468 and is well suited for any analyte for which a binding partner can be found or produced. It is particularly advantageous for detection of the following classes of analytes: the drugs of abuse, the various therapeutic and prophylactic pharmaceutical agents, hormones, microorganisms (including viruses) and antibodies to microorganisms for which antigens or antigenic determinants can be produced.

Alternatively, in an indirect capture variation, the length of the column of color may be directly proportional to the concentration of analyte in the test sample by immobilizing in the capture zone 34 a second distinct ligand capable of binding the analyte. For example, the capture zone 34 can contain a second anti analyte antibody immobilized therein, and the conjugate zone 32 can contain an excess amount of a solulizable enzyme:-first antibody complex (conjugate).

In this variation, all analyte passing through the conjugate zone 32 becomes labeled by complexing with the excess conjugate. Thereafter, enzyme labeled analyte passes to the capture zone 34 and becomes immobilized on the stationary phase by forming an antibody:analyte:conjugate sandwich with the immobilized second antibody. Because this immobilized analyte bears an enzyme label from the conjugate zone, the amount of enzyme passing to the substrate zone 18 is inversely related to the amount of analyte present in the sample. As previously indicated, as less enzyme label passes to the substrate zone, the transformable substrate is depleted more slowly and the column of signal is longer. Conversely, as more enzyme label passes to the substrate zone 18, the enzyme depletion occurs more rapidly and a shorter column of signal is produced. Accordingly, high and low analyte concentrations in the test sample are associated with long and short columns of signal, respectively, thereby providing a direct relationship between the length of the column and the concentration of analyte in the test sample.

This method is particularly well suited for analyzing larger molecular weight antigens and macromolecules which have more than one antigenic site per molecule. Illustrative macromolecules include human chorionic gonadatropin (hCG), follicle stimulating hormone (FSH), luteinizing hormone (LH), thyroid stimulating hormone (TSH) and the like.

Preferably, the conjugate zone 32 and the capture zone 34 are separated (not shown) to prevent the enzyme conjugate from becoming immediately trapped at the interface of the two zones prior to its reaction with the analyte. Also, it is preferred that zone 32 or both zones 32 and 34 be buffered at a pH that maintains or optimizes the affinity between the analyte and the conjugate. Preferably, the pH ranges from about 5.5 to about 10.5, more preferably from about 6.5 to about 9.8. As in the first embodiment, buffer may be present in the wicking solution 11 or it may be dried or impregnated into the conjugate zone 32.

It is possible that enzyme label be selected so that it is active within the pH range of the buffer selected. For example, the enzyme label may be alkaline phosphatase, and the buffer pH range may be from 9.4 to about 9.8. Alternatively, the accessory zone 22 contains a second solulizable buffer dried or impregnated therein. The second buffer is selected to adjust the local pH to an optimum compatible with the enzyme of interest. In this manner, the pH optimum of the enzyme need not be the same as the pH optimum of the analyte conjugate affinity reactions.

C. Methods of Use

In addition to the device mentioned above, the present invention further relates to a method for quantitating the activity of an enzyme. The activity quantitated, in turn, can be related to the concentration of an enzyme analyte, or to the concentration of a non-enzyme analyte which can be complexed with an enzymatic label.

The method of quantitating the activity of an enzyme employs a test strip device 10 such as that described above, and comprises the steps of:

(a) contacting the proximal end of the test strip with an aqueous test sample and allowing the test sample to migrate to the quantitation zone; and (b) determining the amount of signal produced in the quantitation zone as a measure of the enzyme activity.

The contacting of step (a) includes pipetting, spotting, wicking, exposing to a fluid stream or dipping the proximal end of the test strip 10, 30 into the test sample or a solution including the test sample. This step may also serve to solubilize a reagent. For example, when a small volume of sample is pipetted onto the test strip, it may be pipetted directly onto the first reagent zone 22,32 to facilitate solubilization of the reagent.

Preferably, after contacting the sample to the proximal end of the bibulous test strip, the test strip's proximal end 12 is contacted with a wicking solution 11 which facilitates migration. The wicking solution is preferably buffered at a pH selected to optimize the reactions in the zone, as previously described. The buffer can be added directly to the wicking solution, or can be solubilized from a reagent zone 22, 32 by the mobile phase. After the proximal end of the bibulous test strip is contacted with the aqueous test sample and, optionally, a wicking solution, migration of the aqueous phase is allowed to proceed toward the distal end 14 of the test strip.

The next step in the method, determining the activity of the enzyme in the test sample, is accomplished either by measuring the length of the column of signal 42 or 52, or by measuring the intensity of the column of signal. The former method is preferred since it does not require elaborate instrumentation. The latter method typically does require instrumentation if more than semi-quantitative results are required. Alternatively, by running several standards of known enzyme activity, a calibration curve is created, wherein the enzyme activity in the unknown test samples can be obtained from the calibration curve. Test samples with enzyme activities greater than the working range of the test strip are typically diluted 1:10 with 0.9% NaCl and rerun.

An optional further step involves relating the enzyme activity to the concentration of the enzyme in the test sample.

The second embodied device 30 may be used to determine a non-enzyme analyte which is conjugated to an enzyme label. This method comprises quantitating the activity of an enzyme label which is conjugated directly or indirectly to the analyte of interest; and relating the enzyme activity to the concentration of the analyte. The quantitating step is accomplished by measuring the length or intensity of the column of signal 62, 72 as previously described. The relating step correlates the enzyme activity to the concentration of analyte in the sample and depends on the configuration of the capture zone 34.

The present invention also provides for a kit comprising any solid phase device 10, 30 embodied herein and reagents, including a wicking solution 11. A scale 80 calibrated with gradations 82 may optionally be incorporated in a rectangular transparent plastic housing (not shown) along with the solid phase device or as a separate component. The gradations 82 correlate the length of the column of signal to enzyme concentration and/or to analyte concentration.

The following example is given by way of illustration only and should not be construed as limiting the spirit or scope of the invention as, based upon this disclosure, many variations will become obvious to those of ordinary skill in the art.

EXAMPLE 1

Linear Reading System For Alkaline Phosphatase

Sample Preparation

Aliquots of a stock solution of alkaline phosphatase (Sigma Chemical, St. Louis, #P 6774) STRENGTH] were diluted into an aqueous solution comprising 100 mM glycine, 1 mM $MgCl_2$, 0.1 mM $ZnCl_2$ at pH 10.5 to produce solutions having approximately the following relative concentrations of alkaline phosphatase activity: 0 U/ml; 2 U/ml; 5 U/ml; 50 U/ml and 500 U/ml

Strip Preparation

Strips were created by adhering matrix segments together in fluid communication adjacent one another on an adhesive support in the following order to form sheets:

a 65 mm wide strip of untreated Whatman #1 filter paper as part of the quantitation zone;

a 5 mm wide strip of Whatman #1 filter paper impregnated with a 1 mg/ml solution of 3-indoxyl phosphate (Sigma Chemical, St Louis, #I 5505) followed by lyophilization, as the substrate zone;

a 5 mm wide strip of untreated Whatman #1 filter paper as a wick.

The sheets were then cut transversely into multiple strips 75 mm long by about 1.5 mm wide, with the wick defining the proximal end and the quantitation zone defining the distal end.

Alternatively, pre-cut strips can be formed by impregnating a substrate zone of desired length near the proximal end of the strip.

Assay Protocol

The proximal (wick) end of the test strip was inserted in an aqueous solution (test sample) having 500 U/ml of alkaline phosphatase activity. After 5 min. at room temperature, the aqueous solution (mobile phase) ascended to the distal end of the test strip.

The above procedure was repeated for each of the sample alkaline phosphatase solutions prepared above.

Results

A blue column of color was produced by the transformed (precipitated) substrate, wherein the alkaline phosphatase activity in the test sample was inversely proportional to the length of the column of color as shown in Table I below. The reported $R_f$ is the ratio of the measured length of color to the 70 mm length of the quantitation zone. The series of alkaline phosphatase standards which were run by the above assay method produced a calibration curve which was used to determine the alkaline phosphatase activity of subsequent unknown samples.

TABLE I

| Sample Concentration (units/ml) | Length of column of color (mm) | $R_f$ value |
| --- | --- | --- |
| 0 | no color | n/a |
| 2 | 38 | .54 |
| 5 | 32 | .46 |
| 50 | 18 | .26 |
| 500 | 12 | .17 |

What is claimed is:

1. A method of quantitating an enzyme in a test sample, comprising the steps of:
   (a) contacting the test sample to a bibulous test strip through which the test sample migrates, said test strip comprising,
      (i) a proximal end and a distal end, said proximal end for receiving the test sample with sample transport ending at or before said distal end;
      (ii) a substrate zone disposed between the proximal and distal ends and containing a depletable quantity of a transformable enzyme substrate, with the proviso that said substrate is soluble in and transported by said aqueous mobile phase along said strip until substantially all of said substrate is transformed to an insoluble, nondiffusive reaction product thereby ending the enzyme/substrate reaction; and
      (iii) a quantitation zone disposed between said proximal end and the distal end wherein said quantitation zone is free of immobilization reagents and wherein said reaction product ceases transport through the test strip thereby producing a column of signal in said quantitation zone; and
   (b) detecting the length and intensity of the column of signal produced in the quantitation zone as a measure of the enzyme activity.

2. The method according to claim 1 wherein said enzyme is selected from the group consisting of alkaline phosphatase, acid phosphatase, β-galactosidase, β-D-glucosidase, horseradish peroxidase and aryl sulfatase.

3. The method according to claim 1 including the additional step comprising contacting said proximal end of said bibulous test strip with a wicking solution following the contact of the test sample to said proximal end.

4. The method according to claim 1 wherein determining the amount of signal produced comprises measuring the length of the column of signal and inversely relating said length to enzyme activity.

5. The method according to claim 1 wherein determining the amount of signal produced comprises measuring the intensity of the column of signal and relating said intensity to enzyme activity.

6. A method of quantitating an analyte in a sample, said analyte being directly or indirectly coupleable to an enzyme label, comprising:
   (a) quantitating the activity of the enzyme according to the method of claim 1; and
   (b) relating the enzyme activity to the amount of analyte present in the sample.

7. A chromatographic slid phase device for quantitating the activity of an enzyme in a sample, said device comprising a bibulous test strip through which the test sample migrates, said test strip having:
   a proximal end and a distal end, said proximal end for receiving the test sample with sample transport ending at or before said distal end;
   and including at least two zones:
      (a) a substrate zone disposed between the proximal and distal ends and containing a depletable quantity of a transformable enzyme substrate, with the proviso that said substrate is soluble in and transported by said aqueous mobile phase along said strip until substantially all of said substrate is transformed to an insoluble, nondiffusive reaction product; and
      (b) a quantitation zone disposed between said proximal end and the distal end wherein said quantitation zone is free of immobilization reagents and wherein said reaction product ceases transport through the test strip thereby producing a column of signal in said quantitation zone, the amount of signal being related to the activity of said enzyme, wherein the length of the column of signal is inversely proportional to enzyme activity and intensity of signal is directly proportional to enzyme activity.

8. The device according to claim 7 wherein said enzyme is selected from the group consisting of alkaline phosphatase, acid phosphatase, β-galactosidase, β-D-glucosidase, horseradish peroxidase and aryl sulfatase.

9. The device according to claim 7 wherein said enzyme is alkaline phosphatase or acid phosphatase and said transformable enzyme substrate is 3-indoxyl phosphate.

10. The device according to claim 7 wherein the column of detectible signal comprises a column of color, the length of which is proportional to the enzyme activity.

11. The device according to claim 7 wherein the transformed substrate becomes immobilized by being transformed to a chromophore which is insoluble in the aqueous phase.

12. The device according to claim 7 wherein the transformed substrate becomes immobilized covalently by being transformed to a reactive compound which couples with a compound covalently bound to the test strip in the quantitation zone.

13. The device according to claim 7, wherein said test strip further comprises an capture zone disposed between said proximal end and said substrate zone for selectively passing enzyme labeled analyte to the substrate zone such that the enzyme activity quantitated in the quantitation zone is related to the amount of analyte.

14. The device according to claim 7, and further comprising an indicator zone near the distal end for indicating when the mobile phase has reached said indicator zone.

15. A kit comprising the solid phase device of claim 7, a wicking solution for causing migration of aqueous sample components to the quantitation zone, and a scale for measuring the length of the column of signal as a measure of enzyme activity.

* * * * *